United States Patent [19]

Giannessi et al.

[11] Patent Number: 5,192,759
[45] Date of Patent: Mar. 9, 1993

[54] DERIVATIVES OF 1,2,3,4-TETRAHYDRONAPHTYLAMINE ENDOWED WITH NOOTROPIC ACTIVITY AND PHARMACEUTICAL COMPOSITIONS CONTAINING SAME

[75] Inventors: Fabio Giannessi; Orlando Ghirardi; Domenico Misiti; Maria O. Tinti; Roberto Cozzolino, all of Rome, Italy

[73] Assignee: Sigma-Tau Industrie Farmaceutiche Riunite S.p.A., Rome, Italy

[21] Appl. No.: 809,874

[22] Filed: Dec. 18, 1991

[30] Foreign Application Priority Data

Dec. 21, 1990 [IT] Italy .................. 48605 A/90

[51] Int. Cl.$^5$ .................. C07D 223/10; A61K 31/55
[52] U.S. Cl. .................. 514/212; 514/319; 514/424; 514/425; 540/526; 540/531; 540/485; 546/195; 548/543; 548/544; 548/551; 562/443
[58] Field of Search .................. 540/526, 531, 485; 546/195; 548/543, 544, 551; 514/212, 319, 424, 425

[56] References Cited

U.S. PATENT DOCUMENTS 3,238,223 3/1966 Wilson et al. .................. 548/543

Primary Examiner—Robert T. Bond
Attorney, Agent, or Firm—Allegretti & Witcoff, Ltd.

[57] ABSTRACT

1,2,3,4-tetrahydronaphthlamines of formula (1)

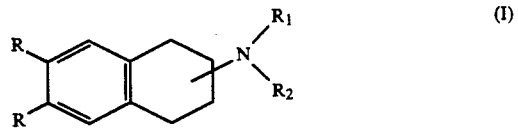

(I)

wherein
R is H or $OCH_3$;

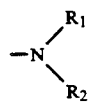

is either at 1 or 2 position
$R_1$ is H;
$R_2$ is selected from:
  L-prolyl, optionally N-substituted with acetyl or carbobenzoxy,
  L-pyroglutamyl,
  (pyrrolidin-2-one-1-yl)acetyl,
  3-carboxy-2-hydroxypropyl:

or $R_1$ and $R_2$ taken together with the nitrogen atom form the ring

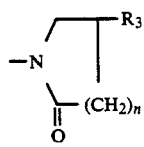

wherein n=1,2,3 and $R_3$—H, OH are nootropic substances potent enhancers of learning processes and memory.

Orally or parenterally administrable pharmaceutical compositions in unit dosage form comprise between about 100 and about 500 mg of a compound of formula (1).

4 Claims, No Drawings

DERIVATIVES OF 1,2,3,4-TETRAHYDRONAPHTYLAMINE ENDOWED WITH NOOTROPIC ACTIVITY AND PHARMACEUTICAL COMPOSITIONS CONTAINING SAME

SUMMARY OF THE INVENTION

The present invention relates to 1,2,3,4-tetrahydronaphtylamines of formula (I)

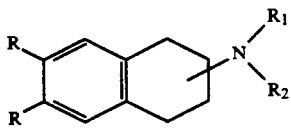

wherein
R is H or $OCH_3$;

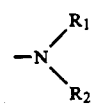

is either at 1 or 2 position
$R_1$ is H;
$R_2$ is selected from:
 L-prolyl, optionally N-substituted with acetyl or carbobenzoxy,
 L-pyroglutamyl,
 (pyrrolidin-2-one-1-yl)acetyl,
 3-carboxy-2-hydroxypropyl;
or $R_1$ and $R_2$ taken together with the nitrogen atom form the ring

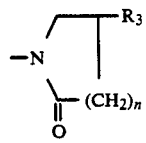

wherein n=1,2,3 and $R_3$=H, OH.

The compounds of formula (I) are nootropic substances potent enhancers of learning processes and memory.

The present invention also relates to orally or parenterally administrable pharmaceutical compositions for enhancing the learning processes and memory, comprising a compound of formula (I) as active ingredient.

Because of the presence of at least one chiral carbon atom (the carbon atom bound to $-NR_1R_2$), the compound of formula (I) can exist as two enantiomers designated (R) and (S); since the $R_2$ group can contribute a further chiral center, the compounds of formula (I) can also exist as diastereomers; in both cases, the compounds of formula (I) can also exist as racemic mixtures. Since it has been found that both the optically active forms and the racemic mixtures are pharmacologically active, hereinbelow, for the sake of semplicity, no specific reference to the optical activity of the compounds shall be made.

DESCRIPTION OF THE PRIOR ART

Distrubances of the processes of learning and memory may become manifest in any patient, regardless of age. These disturbances can be secondary to several pathologles or traumas; alternatively, they can be brought about by the normal process of aging. For this reason, the increase in life expectancy and the attendant increase in number of elderly people have prompted the development of novel methods and drugs for treating disorders of learning and memory.

Drugs for treating amnesia, such as piracetam, are already known, (see e.g. Curr. Dev. Psicopharmacol., 3, 22, 1976).

The compounds of formula (I) are not structurally related to either piracetam or other known nootropic agents.

Derivatives of 2-amino-6,7-dimethoxytetraline that from a structural viewpoint are vaguely related to the compounds of the present invention are disclosed in EP-A-0 273 017.

However, these known compounds are endowed with anti-hypertensive activity which in no way can be related to the nootropic activity that the compounds of the present invention exhibit in enhancing the processes of learning and memory. Therefore, in order to asses their nootropic activity, the compounds of formula (I) were compared with piracetam in some experimental models and were shown to be more potent than the reference compound.

DETAILED DESCRIPTION OF THE INVENTION

The compounds of formula (I) can be prepared via known condensation procedures.

The compounds of formula (I) wherein R is either hydrogen or methoxy,

is at position 2
$R_1$=H
$R_2$=
 L-prolyl
 L-pyroglutamyl,
 (pyrrolidin-2-one-1-yl) acetyl, or
 3-carboxy-2-hydroxy-propyl
can be prepared via the following reaction scheme, wherein, as an example, R is $OCH_3$:

Scheme 1

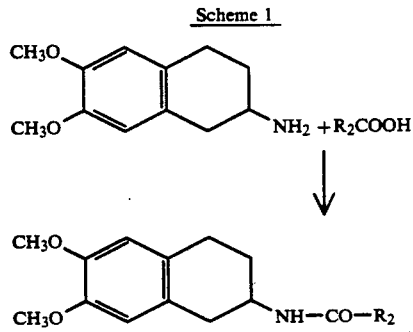

The condensation of 1,2,3,4-tetrahydro-6,7-dimethoxy-2-naphtylamine (ST 690) (described in J. Med. Chem. 21/8, 825, 1978) with $R_2$—COOH is carried out in an anhydrous inert organic solvent such as $CH_3CN$ or $CH_2Cl_2$ or in an organic solvent-water mixture in the presence of a condensating agent such as DCC (dicyclohexylcarbodiimide), CDI (carbonyldiimidazole), EEDQ (2-ethoxy-1-ethoxy-carbonyl-1,2-dihydroquinoline).

The reaction mixture is kept under stirring at a temperature comprised between 18° and 35° C., preferably at 25° C., for reaction times comprised between 8 and 48 hours, preferably 20 hours.

The desired product is isolated by concentrating the reaction mixture under vacuum, taking up the residue in an organic solvent such as acetonitrile or methylene chloride, and precipitating with ethyl ether.

In order to prepare the compounds wherein

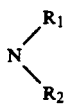

form a ring, the reaction can be carried out according to the following scheme:

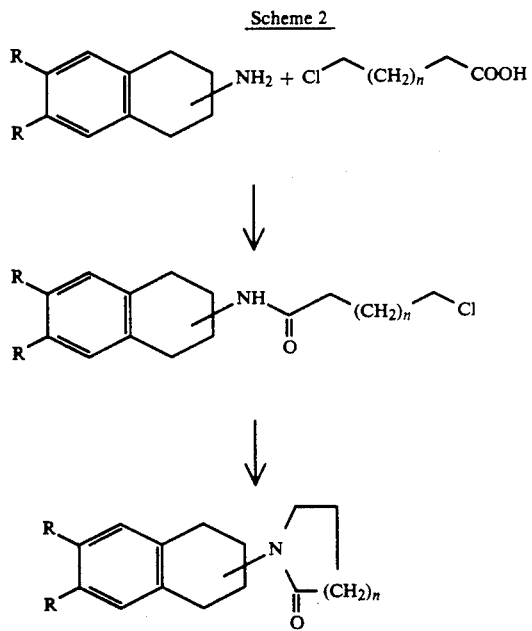

Scheme 2

The condensation reaction of 1,2,3,4-tetrahydronaphtyl-amine with the ω-chlorocarboxylic acid, e.g. 4-chlorobutyric acid, is carried out with the same procedures as those described in connection with Scheme 1. The reaction product thus obtained is isolated and treated with NaH in an anhydrous inert organic solvent such as acetonitrile or methylene chloride, at a temperature comprised between 20° and 30° C., for reaction times comprised between 20 and 48 hours.

The desired product is isolated by precipitation from the reaction mixture followed by silica gel chromatography using a gradient of ethyl acetate or ethyl acetate-hexane as eluant.

Particularly preferred compounds of formula (I) are e.g. the following:

N-(L-pyroglutamyl)-1,2,3,4-tetrahydro-6,7-dimethoxy-2-naphtylamine;

N-[(pyrrolidin-2-one-1-yl)acetyl]-1,2,3,4-tetrahydro-6,7-dimethoxy-2-naphtylamine;

N-(benzyloxycarbonyl-L-prolyl)-1,2,3,4-tetrahydro-6,7-dimethoxy-2-naphtylamine;

N-(L-prolyl)-1,2,3,4-tetrahydro-6,7-dimethoxy-2-naphtylamine;

N-(N-acetyl-L-prolyl)-1,2,3,4-tetrahydro-6,7-dimethoxy-2-naphtylamine;

1-(1,2,3,4-tetrahydro-6,7-dimethoxy-2-naphtyl)-4-hydroxy-pyrrolidin-2-one;

1-(1,2,3,4-tetrahydro-6,7-dimethoxy-2-naphtyl)-pyrrolidin-2-one;

1-(1,2,3,4-tetrahydro-1-naphtyl)-pyrrolidin-2-one;

N-(L-pyroglutamyl)-1,2,3,4-tetrahydro-6,7-dimethoxy-1-naphtylamine;

N-[(pyrrolidin-2-one-1-yl)acetyl]-1,2,3,4-tetrahydro-6,7-dimethoxy-1-naphtylamine;

N-(benzyloxycarbonyl-L-prolyl)-1,2,3,4-tetrahydro-6,7-dimethoxy-1-naphtylamine;

N-(L-prolyl)-1,2,3,4-tetrahydro-6,7-dimethoxy-1-naphtylamine;

N-(N-acetyl-L-prolyl)-1,2,3,4-tetrahydro-6,7-dimethoxy-1-naphtylamine;

1-(1,2,3,4-tetrahydro-6,7-dimethoxy-1-naphtyl)-4-hydroxy-pyrrolidin-2-one;

1-(1,2,3,4-tetrahydro-6,7-dimethoxy-1-napthyl)-pyrrolidin-2-one;

1-(1,2,3,4-tetrahydro-6,7-dimethoxy-2-napthyl)-piperidin-2-one;

1-(1,2,3,4-tetrahydro-6,7-dimethoxy-1-naphtyl)-piperidin-2-one;

1-(1,2,3,4-tetrahydro-6,7-dimethoxy-2-naphtyl)-5-hydroxy-piperidin-2-one;

1-(1,2,3,4-tetrahydro-6,7-dimethoxy-2-naphtyl)-ε-caprolactam;

1-(1,2,3,4-tetrahydro-6,7-dimethoxy-2-naphtyl)-5-hydroxy-ε-caprolactam;

1-(1,2,3,4-tetrahydro-6,7-dimethoxy-1-naphtyl)-εcaprolactam;

1-(1,2,3,4-tetrahydro-6,7-dimethoxy-1-naphtyl)-5-hydroxy-ε-caprolactam;

1-(1,2,3,4-tetrahydro-1-naphtyl)-4-hydroxy-pyrrolidin-2-one.

The following non-limiting examples illustrate the preparation of some compounds of the present invention.

EXAMPLE 1

Preparation of N-(L-pyroglutamyl)-1,2,3,4-tetrahydro-6,7-dimethoxy-2-naphtylamine (ST 703)

To L-pyroglutamic acid (1 g, 7.7 mmoles) in CH$_3$CN (80 mL), 1,2,3,4-tetrahydro-6,7-dimethoxy-2-naphtylamine (1.59 g, 7.7 mmoles) and EEDQ (2.85 g, 11 mmoles) were added under stirring. To the resulting mixture water was added till complete solubilization and the solution was kept at room temperature under stirring for 20 hours. The solvent was evapored and the residue taken up with CHCl$_3$. Et$_2$O was added under stirring. The solid which formed was filtered off giving 2 g of the title compound. Yield 81%.

M.P. = 195°–196° C. $[\alpha]_D^{25} = +3°$ MeOH (c=0.5)

Silica gel TLC; Eluant EtOAc-MeOH 9:1. RF=0.17

Elementary analysis for C$_{17}$H$_{22}$N$_2$O$_4$: Calculated: C 64.13, H 6.96, N 8.79; Found: C 63.9, H 6.86, N 8.66.

$^1$HNMR (CDCL$_3$): δ7.30 (br, 1H, —NH CHOCH$_2$—), 6.8 (br, 1H, —NHCOCH—), 6.58 (s, 1H, aromatic), 6.5 (s, 1H, aromatic), 4.30–4.20 (m, 1H, —COCHN—), 4.20–4.12 (m, 1H, —CHNCO—), 3.82 (s, 6H, 2—OCH$_3$), 3.08-2.98 (m, 1H, —CHHCHCH$_2$CH$_2$—), 2.92-2.70 (m, 2H, —CH$_2$CH$_2$CHCH$_2$—), 2.65-1.65 (m, 7H, —CHHCHCH$_2$CH$_2$—, —NCOCH$_2$CH$_2$—)

HPLC: μBondapak-C$_{18}$; L=300 mm; inner diameter=3.9 mm; size=10 μm; Eluant=CH$_3$CN/KH$_2$PO$_4$0.05M (22.5:77.5); Flow rate=1 mL/min; Permanence time=9.71 min.

EXAMPLE 2

Preparation of
N-[(pyrrolidin-2-one-1-yl)acetyl]-1,2,3,4-tetrahydro-6,7-dimethoxy-2-naphtylamine (ST 706)

Prepared following the procedures of Example 1, starting from (pyrrolidin-2-one-1-yl) acetic acid. Yield 80%.

M.P.=150°-151° C.

Silica gel TLC; Eluant EtOAc-McOH 7:3. RF=0.57

Elementary analysis for C$_{18}$H$_{24}$N$_2$O$_4$: Calculated: C 65.04, H 7.27, N 8.42; Found: C 64.46, H 7.21, N 8.30.

$^1$HNMR (CDCl$_3$): δ6.6 (s, 1H, aromatic), 6.5 (s, 1H, aromatic), 6.25 (br, 1H, —CONH—), 4.30-4.18 (m, 1H, —CHNCO—), 3.9 (s, 2H, —COCH$_2$NCO—), 3.85 (s, 6H, 2—OCH$_3$), 3.6-3.42 (m, 2H, —CH$_2$NCO—), 3.8-2.95 (m, 1H, —CHCHCH$_2$CH$_2$—), 2.90-2.70 (m, 2H, —CH$_7$CH$_2$CHCH$_2$—), 2.65-2.52 (m, 1H, —CHHCHCH$_2$CH$_2$—), 2.40 (t, 2H, —COCH$_2$CH$_2$—), 2.12-1.64 (m, 4H, —CH$_2$CH$_2$CHCH$_2$—, —COCH$_2$CH$_2$—)

HPLC: μBendapak-NH$_2$; L=300 mm; inner diameter=3.9 mm; size=10 μm; Eluant=CH$_3$CN/KH$_2$PO$_4$ 0.05M (65:35); Flow rate=1 mL/min; Permanence time=3.13 min.

EXAMPLE 3

Preparation of
N-(benzyloxycarbonyl-L-prolyl)-1,2,3,4-tetrahydro-6,7-dimethoxy-2-naphtylamine (ST 705)

Prepared following the procedures of Example 1, starting from Z-L-proline. Yield 85%.

M.P.=152°-153° C. [α]$_D^{25}$=−35° MeOH (c=1)

Silica gel TLC; Eluant EtOAc-MeOH 9:1. RF=0.76

Elementary analysis for C$_{25}$H$_{30}$N$_2$O$_5$: Calculated: C 68.47, H 6.89, N 6.38; Found: C 68.49H 6.85, N 6.34.

$^1$HNMR (CDCl$_3$): δ7.35 (s, 5H, aromatic), 6.8 (br, 1H, —NHCO—), 6.58 (s, 1H, aromatic), 6.5 (s, 1H aromatic), 5.1 (s, 2H, —CH$_2$Ph), 4.32-4.22 (m, 1H, —COCHN—), 4.22-4.10 (m, 1H, —CHNCO—), 3.92 (s, 6H, 2—OCH$_3$), 3.6-3.38 (m, 2H, —CH$_2$NCO—), 3.05-2.90 (m, 1H, CHHCHCH$_2$CH$_2$—), 2.90-2.70 (m, 2H, —CH$_2$CH$_2$CHCH$_2$—), 2.65-2.50 (m, 1H, —CHHCHCH$_2$CH$_2$—), 2.48-1.65 (m, 6H, —CH$_2$CH$_2$CHCH$_2$—, CONCH$_2$CH$_2$CH$_2$—)

HPLC: μBondapaK C$_{18}$; L=300 mm; inner diameter=3.9 mm; size=10 μm; Eluant=CH$_3$CN/KH$_2$PO$_4$ 0.05M (45:55); Flow rate=1 mL/min; Permanence time=6.51 min.

EXAMPLE 4

Preparation of
N-(L-prolyl)-1,2,3,4-tetrahydro-6,7-dimethoxy-2-naphtylamine (ST 716)

To ST 705 (7.5 g, 17.1 mmoles) in MeOH (60 mL), 10% Pd/C (0.75 g) was added. The resulting mixture was hydrogenated in a PARR hydrogenator at 40 psi for 2 hours. The mixture was filtered through celite and the filtrate brought to dryness. The residue was chromatographed on silica gel using CHCl$_3$—MeOH 95:5 as eluant, 3.7 g of the title compound were obtained. Yield 71%.

M.P.=108°-109° C. [α]$_D^{25}$=−31.5° MeOH (c=1)

Silica gel TLC; Eluant CHCl$_3$—MeOH 8:2. RF=0.5

Elementary analysis for C$_{17}$H$_{24}$N$_2$O$_3$: Calculated: C 67.08, H 7.95, N 9.20; Found: C 67.40, H 8.20, N 9.30.

$^1$HNMR (CDCl$_3$): δ7.85 (br, 1H, —NHCO—), 6.6 (s, 1H, aromatic), 6.55 (s, 1H, aromatic), 4.15-4.05 (m, 1H, —CHNCO—), 3.92 (s, 6H, 2—OCH$_3$), 3.88-3.7 (m, 1H, —COCHN—), 3.07-2.95 (m, 2H, —CHHCHCH$_2$CH$_2$—, NCHHCH$_2$—), 2.95-2.70 (m, 3H, —CH$_2$CH$_2$CHCH$_2$—, —NCHHCH$_2$—), 2.65-2.50 (m, 1H, —CHHCHCH$_2$CH$_2$—), 2.20-1.62 (m, 7H, —CH$_2$CH$_2$CHCH$_2$—, NHCH$_2$CH$_2$CH$_2$—)

HPLC: TECHSIL 5 NH$_2$; L=300 mm; inner diameter=3.9 mm; Eluant=CH$_3$CN/KH$_2$PO$_4$ 0.05M (65:35); Flow rate=1 mL/min; Permanence time=3.13 min.

EXAMPLE 5

Preparation of N-(N-acetyl L-prolyl)-1,2,3,4-tetrahydro-6,7-dimethoxy-2-napthylamine (ST 729)

To acetic acid (453 mg, 7.75 mmoles) in CH$_3$CN (50 mL), ST 716 (2.3 g, 7.75 mmoles) and EEDQ (2.87 g, 11.62 mmoles) were added under stirring and the resulting mixture was kept at room temperature under stirring for 20 hours. Following solvent evaporation, the residue was chromatographed on silica gel using EtOAc—MeOH (95:5) as eluant. The title compound was obtained with a yield of 46%.

M.P.=63°-65° C. [α]$_D^{25}$=−39.3° MeOH (c=1)

Silica gel TLC; Eluant EtOAc—MeOH 8:2. RF=0.44.

Elementary analysis for C$_{19}$H$_{26}$N$_2$O$_4$: Calculated: C 65.8, H 7.5, N 8.0; Found: C 65.3, H 7.83, N 8.24.

$^1$HNMR (CDCl$_3$): δ7.15 (br, 1H, —NHCO—), 6.58 (s, 1H, aromatic), 6.5 (s, 1H, aromatic), 4.55-4.45 (m, 1H, —COCHN—), 4.2-4.05 (m, 1H, CHNCO—), 3.91 (s, 6H, 2—OCH$_3$), 3.60-3.38 (m, 2H, —CH$_2$NCO—), 3.05-2.92 (m, 1H, —CHHCHCH$_2$CH$_2$—), 2.90-2.70 (m, 2H, —CH$_2$CH$_2$CHCH$_2$—), 2.66-2.53 (m, 1H, —CHHCHCH$_2$CH$_2$), 2.48-1.65 (m, 9H, —CH$_2$CH$_2$CHCH$_2$—, CH$_3$CONCH$_2$CH$_2$CH$_2$—)

HPLC: μBondapak C$_{18}$; L=300 mm; inner diameter=3.9 mm; size=10 μm; Eluant=KH$_2$PO$_4$ 0.05 M/CH$_3$CN (65:35); Flow rate=1 mL/min; Permanence time=6.00 min.

EXAMPLE 6

Preparation of
1-(1,2,3,4-tetrahydro-6,7-dimethoxy-2-naphtyl)-4-hydroxypyrrolidin-2-one (ST 618)

To N-(3-carboxy-2-hydroxypropyl)-1,2,3,4-tetrahydro-6,7-dimethoxy-2-naphtylamine hydrocloride (ST 576, prepared as described in the Italian patent application 47652A/88) (1 g, 2.89 mmoles) in xylene (40 mL), 1.2 mL HMDS and TMSCI (few drops) were added. The resulting mixture was refluxed under stirring for 24 hours. Xylene was evaporated, the residue was taken up with EtOH (40 mL) and 1N HCl in isopropanol (1 mL) was added thereto. After 5 minutes, NaHCO$_3$ was added till neutrality, the mixture was filtered and the filtrate evaporated. The residue was chromatographed on silica gel using EtOAc—MeOH (95:5) as eluant. 600 mg of the title compound were obtained. Yield 71%.

M.P.=178°-179° C.

Silica gel TLC; Eluant EtOAc—MeOH 8:2. RF=0.5.

Elementary analysis for $C_{16}H_{21}NO_4$: Calculated: C 65.96, H 7.26, N 4.80; Found: C 65.4, H 7.21, N 4.88.

$^1$HNMR (CDCl$_3$): δ6.6–6.5 (m, 2H, aromatic), 4.58–4.5 (m, 1H, CHOH), 4.5–4.35 (m, 1H, —CH NCO—), 3.92 (s, 6H, 2—OCH$_3$), 3.70–3.58 (m, 1H, —CHHNCO—) 3.38–3.30 (m, 1H, —CHHNCO—), 2.98–2.70 (m, 5H, —COCHH—, —CH$_2$CHCH$_2$CH$_2$—), 2.6 (br, 1H, —OH), 2.48–2.40 (m, 1H, COCHH—), 2–1.6 (m, 2H, —CHCH$_2$CH$_2$—).

HPLC: Lichrosorb RP$_{18}$; L=250 mm; inner diameter=4 mm; size=10 μm; Eluant=KH$_2$PO$_4$ 0.05 M/CH$_3$CN (85:15); Flow rate=1.5 mL/min; Permanence time=15.70 min.

EXAMPLE 7

Preparation of 1-(1,2,3,4-tetrahydro-6,7-dimethoxy-2-naphtyl)-pyrrolidin-2-one (ST 769)

To 4-chlorobutyric acid (3.25 g, 26.5 mmoles) in CH$_3$CN (200 mL), 1,2,3,4-tetrahydro-6,7-dimethoxy-2-naphtlyl-amine (5.5 g, 26.5 mmoles) and EEDQ (6.65 g, 26.5 mmoles) were added and the resulting solution was kept at room temperature under stirring for 40 hours. The solvent was then evaporated and the residue taken up with CHCl$_3$. Et$_2$O was added thereto under stirring. Following filtration, the filtrate was kept at 0° C. overnight. 3 g (9.6 mmoles) N-(4-chlorobutyroyl)-1,2,3,4-tetrahydro-6,7-dimethoxy-2-naphtylamine were filtered off (silica gel TLC; eluant EtOAc RF=0.64) and dissolved in CH$_3$CN (100 mL). 80% NaH in mineral oil (520 mg. 17.3 mmoles) was added in two portions, the second portion after some hours following the first one.

The resulting mixture was kept at room temperature under stirring for 2 days. The mixture was filtered, the filtrate evaporated and the residue chromatographed on silica gel using EtOAc as eluant. 2 g of the title compound were obtained. Last step yield: 75%. Overall yield 27%.

M.P.=98°–99° C.

Silica gel TLC; Eluant EtOAc. RF=0.28.

Elementary analysis for $C_{16}H_{21}NO_3$: Calculated: C 69.79, H 7.68, N 5.08; Found: C 70.05, H 7.86, N 4.58.

$^1$HNMR (CDCl$_3$): δ6.6, (s, 1H, aromatic), 6.52 (s, 1H aromatic), 4.45–4.32 (m, 1H, —CHNCO—), 3.92 (s, 6H, 2—OCH$_3$), 3.4 (t, 2H, CH$_2$NCO—), 3.0–2.7 (m, 4H, —CH$_2$CHCH$_2$CH$_2$—), 2.4 (t, 2H, —CH$_2$CON—), 2.1–1.75 (m, 4H, —CH$_2$CHCH$_2$CH$_2$—, —CH$_2$CH$_2$CON—)

HPLC: μBondapak C$_{18}$; L=300 mm; inner diameter=3.9 mm; size=10 μm; Eluant=KH$_2$PO$_4$ 0.05 M/CH$_3$CN (70:30); Flow rate=1 mL/min; Permanence time=12.63 min.

EXAMPLE 8

Preparation of 1-(1,2,3,4-tetrahydro-1-naphtyl)-pyrrolidin-2-one (ST 748)

CDI (6.61 g. 40.75 mmoles) and, after 1 hour, 1,2,3,4-tetrahydro-1-naphtylamine (5 g, 33.96 mmoles) were added to 4-chlorobutyric acid (4.16 g, 33.96 mmoles) in CH$_2$Cl$_2$ (200 mL) under stirring. The resulting solution was kept at room temperature for 40 hours, then washed with 1N HCl, NaHCO$_3$ (saturated solution), H$_2$O, NaCl (saturated solution) and dried over anhydrous Na$_2$SO$_4$. The solvent was evaporated and the residue taken up with CHCl$_3$. Upon addition of Et$_2$O under stirring a precipitate was obtained consisting of 4.5 g (17.87 mmoles) of N-(4-chloro-butyroyl)-1,2,3,4,-tetrahydro-1-naphtylamine (silica gel TLC; Eluant EtOAc-Hexane (1:1), RF=0.7) which was dissolved in CH$_3$CN (100 mL). To the mixture, 80% NaH in mineral oil (804 mg, 26.8 mmoles) was added in two portions, the second portion after some hours following the first one. The mixture was then kept at room temperature under stirring for 2 days. The mixture was then filtered, the filtrate evaporated and the residue chromatographed on silica gel using EtOAc-Hexane (1:1) as eluant. 1.93 g of the title compound were obtained. Last step yield=50%, overall yield 26%.

M.P.=103°–104° C.

Silica gel TLC; Eluant EtOAc-HEXANE (1:1). RF=0.32.

Elementary analysis for $C_{14}H_{17}NO$: Calculated: C 78.10, H 7.96, N 6.50; Found: C 78.28, H 8.02, N 6.60.

$^1$HNMR (CDCl$_3$): δ7.20–6.95 (m, 4H, aromatic), 5.4 (m, 1H, —CHNCO—), 3.25 (m, 1H, —CHHN—), 3.05 (m, 1H, —CHHN—), 2.8 (m, 2H, —CH$_2$CH$_2$CH$_2$CH—), 2.5 (m, 2H, —CH$_2$CON—), 2.1–1.7 (m, 6H—CH$_2$CH$_2$CON—, —CH$_2$CH$_2$CH$_2$CH—)

HPLC: μBondapak C$_{18}$; L=300 mm; inner diameter=3.9 mm; size=10 mm; Eluant=KH$_2$PO$_4$ 0.05 M/CH$_3$CN (70:30); Flow rate=1.5 mL/min; Permanence time=15.98 min.

The activity of the compounds of the invention was assessed in several pharmacological tests. Some of these tests are illustrated hereinbelow. Since no nootropic substance structurally related to the compounds of the present invention is known, piracetam was used as reference standard.

(A) Assessment of the antiamnesic activity

In order to assess the antiamnesic activity the passive avoidance test in mice was used. Amnesia was brought about by administration of scopolamine (cfr. Bammer, Pharmacological investigations of neurotransmitter involvement in passive avoidance responding: a review and some new results. *Neurosci. Biobehav. Rev.*, 6 (3) 247–296, 1982); or by electroconvulsive shock (ECS) (cfr. Banfi et al., A screening method for substances potentially active on learning and memory. *J. Pharmacol. Methods* Vol.: 8 (4) 255–263, 1982).

Male CD1 mice (Charles River, Italy) weighing 25–26 g were used for the scopolamine-induced amnesia test.

Male CD1 mice (Charles River, Germany) fed on a normal diet, were used for the ECS-induced amnesia test.

The compounds were administered i.p.; 0.9 mg/kg in the scopolamine-induced amnesia test; and 9 and 0.9 mg/kg in the ECS-induced amnesia test. All doses were equimolar to piracetam.

The compounds were dissolved in saline. The apparatus for passive avoidance conditioning was a black plastic chamber (42×42 cm, height 40 cm) provided with a floor constructed of metal rods that could be electrified. From the front wall extended a white runway, 30 cm long and 10 cm wide provided with side walls 12 cm high, which led into the box through a guillotine door. The runway was lightened by a 60 W lamp whereas the box remained in the dark (cfr. Ader et al., Retention of passive avoidance response as a function of the intensity and duration of electric shock, *Psychon, Sci.*, 26 (3), 125–127, 1972).

Passive avoidance following scopolamine-induced amnesia

The animals were administered the compounds and scopolamine (1.5 mg/kg s.c.) 30 minutes and 15 minutes, respectively, before the test and were then placed on the runway. After one minute of adaptation, the door was raised and the time employed by the animal to enter the darkened box with all four feet, was recorded.

Upon entry, the guillotine door was lowered and three seconds thereafter the rods were electrified, 0.21 mA for 2 seconds.

Immediately thereafter the animal was placed in the housing cage. Retention was assessed 24 hours later by placing the animal on the runway and again evaluating the latency in entering the chamber, using an endpoint of 300 s (cfr. Bammer, loc. cit.).

Passive avoidance following ECS-induced amnesia 30 minutes following treatment with the compounds, the animals were placed on the runway. After one minute of adaptation, the door was raised and the time employed by the animal to enter the darkened box with all four feet was recorded.

Upon entry, the guillotine door was lowered and three seconds thereafter the rods were electrified, 0.24 mA for 2 seconds.

The mouse was then removed from the chamber and immediately administered an electroshock delivered through spring clips attached to the ears (square wave, intensity 20 mA, amplitude 0.6 msec, duration 0.5 s, frequency 50 Hz).

Immediately thereafter the animal was placed in the housing cage. Retention was assessed 24 hours later by placing the animal on the runway and again evaluating the latency in entering the chamber, using an end-point of 300 seconds (Bammer, loc.cit.).

In each experiment, two groups of animals in addition to the treated ones were used, that were defined as follows:

(1) ceiling control animals (treated with placebo and not subjected to amnesia treatment with scopolamine or ECS) to ensure that these animals not treated with the amnesia agent remembered the task;

(2) base-line control animals (treated with placebo and subjected to amnesia treatment with scopolamine or ECS) to ensure that ECS or scopolamine produced amnesia in the animals not treated with the compounds of the present invention.

The results of each compound under examination were expressed as percentage of amnesia reversal (AR) in order to make comparisons across the tested compounds.

AR is defined as follows: $AR = \frac{CIt}{CIc} \cdot 100$ wherein CI, Comparison Index (the subscripts "t" and "c" refer to "treated" and "ceiling control", respectively) is defined by the formula $CI = [\Sigma Aij/Ni \cdot Nj)]100$ wherein Ni is the number of animals belonging to the i—nth group (ceiling control or treated animals);

Nj is the number of animals belonging to the j—nth group (base-line control animals); and Aij is a binary function that can take only the values +1.0 or −1 depending on whether the latency time (in seconds) of an animal belonging to the i—nth group, Xi, is higher than, the same as or smaller than the latency time (in seconds) of an animal of the j—nth group, Xj.

The sum $\Sigma Aij$ encompasses all the possible pairs obtained by combining each term Xi with each term Xj.

Whenever in performing the test the Comparison Index (CI) between ceiling control animals and baseline control animals, generally expected to range between 60 and 80%, turned out to be lower than 40% the data for the whole experiment were discarded.

The results are shown in Table 1.

TABLE 1

Passive avoidance following scopolamine-induced and ECS induced amnesia
The table shows the ARs of some compounds of the present invention. The number of animals (No.) and the AR of each compound tested at various dose levels are reported.

| | ECS | | | | SCOPOLAMINE | |
|---|---|---|---|---|---|---|
| | 9 mg/kg | | 0.9 mg/kg | | 0.9 mg/kg | |
| | No. | % AR | No. | % AR | No. | % AR |
| Ceiling control group | 56 | 100 | 56 | 100 | 71 | 100 |
| Base-line control group | 114 | 0 | 114 | 0 | 142 | 0 |
| Piracetam | 30 | 0 | 27 | 0 | 34 | 25 |
| ST 618 | 14 | 33 | 24 | 22 | 24 | 56 |
| ST 690 | 12 | 1 | 11 | 12 | 12 | 0 |
| ST 706 | 11 | 28 | 12 | 5 | 12 | 0 |
| ST 716 | 12 | 0 | 12 | 29 | 12 | 16 |
| ST 729 | 12 | 4 | 12 | 4 | 23 | 37 |
| ST 748 | 12 | 61 | 12 | 54 | 12 | 0 |
| ST 769 | 12 | 36 | 12 | 0 | 12 | 0 |

(B) Behavioural profile

The behavioural profile was assessed in male CDI mice (Charles River, Italy) weighing 22–24 g, using the Irwin test (IRWIN S., Drug screening and evaluation procedures; 136, 123–128 1962). The animals had been caged under normal conditions and kept fasting for the last 18 hours. Following administration of the compounds, the behaviour of the animals was monitored for 6 hours.

The compounds were suspended in 10% arabic gum and orally administered at doses equimolar to 90, 23, 5.4 and 1.4 mg piracetam/10 mL/kg of body weight.

The animals of the control groups were administered 10% arabic gum (10 mL/kg, orally).

No compound altered, at the tested doses, the behavioural profile except ST 716 which showed a stimulating effect at doses comprised between 25 and 100 mg/kg, and ST 690 which not only showed a stimulating effect at doses comprised between 25 and 100 mg/kg, but was also toxic (death rate: 50%) at 100 mg/kg.

(C) Analgesic activity

The analgesic activity was assessed in CDI mice (Charles River, Italy) weighing 22–24 g, utilizing the hot plate test (56° C.).

The animals, kept under normal caging conditions and kept fasting for 18 hours, were placed on the hot plate for 30, 60, 120 and 180 minutes following the oral administration of 90, 23, 5.4 and 1.4 mg/10 mL/kg equimolar to piracetam of each compound under examination.

The analgesic activity was assessed by measuring the increase (in seconds) of the time the animals continued to stay on the hot plate. None of the tested compounds was shown to possess analgesic activity.

The compounds of the present invention can be formulated into orally or parenterally administrable pharmaceutical compositions. Suitable excipient and compositions for tablets, vials and like are illustrated in the Canadian patent 1,100,515.

Pharmaceutical compositions in unit dosage form comprise between about 100 and about 500 mg of active ingredient.

What is claimed is:

1. 1,2,3,4-tetrahydronaphtylamine of formula (I)

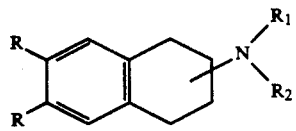

wherein
R is H OCH$_3$;

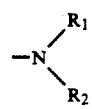

is either at 1 or 2 position
R$_1$ is H;
R$_2$ is selected from:
  L-prolyl, optionally N-substituted with acetyl or carbobenzoxy,
  L-pyroglutamyl,
  (pyrrolidin-2-one-1-yl)acetyl,
  3-carboxy-2-hydroxypropyl;
or R$_1$ and R$_2$ taken together with the nitrogen atom form the ring

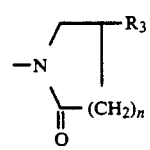

wherein n=1,2,3 and R$_3$=H, OH.

2. A compound of formula I selected from the group consisting of:
N-(L-pyroglutamyl)-1,2,3,4-tetrahydro-6,7-dimethoxy-2-naphtylamine;
N-[(pyrrolidin-2-one-1-yl)acetyl]-1,2,3,4-tetrahydro-6,7-dimethoxy-2-naphtylamine;
N-(benzyloxycarbonyl-L-prolyl)-1,2,3,4-tetrahydro-6,7-dimethoxy-2-naphtylamine;
N-(L-prolyl)-1,2,3,4-tetrahydro-6,7-dimethoxy-2-naphtylamine;
N-(N-acetyl-L-prolyl)-1,2,3,4-tetrahydro-6,7-dimethoxy-2-naphtylamine;
1-(1,2,3,4-tetrahydro-6,7-dimethoxy-2-naphtyl)-4-hydroxy-pyrrolidin-2-one;
1-(1,2,3,4-tetrahydro-6,7-dimethoxy-2-naphtyl)-pyrrolidin-2-one;
1-(1,2,3,4-tetrahydro-1-naphtyl)-pyrrolidin-2-one;
N-(L-pyroglutamyl)-1,2,3,4-tetrahydro-6,7-dimethoxy-1-naphtylamine;
N-[(pyrrolidin-2-one-1-yl)acetyl]-1,2,3,4-tetrahydro-6,7-dimethoxy-1-naphtylamine;
N-(benzyloxycarbonyl-L-prolyl)-1,2,3,4-tetrahydro-6,7-dimethoxy-1-naphtylamine;
N-(L-prolyl)-1,2,3,4-tetrahydro-6,7-dimethoxy-1-naphtylamine;
N-(N-acetyl-L-prolyl)-1,2,3,4-tetrahydro-6,7-dimethoxy-1-naphtylamine;
1-(1,2,3,4-tetrahydro-6,7-dimethoxy-1-naphtyl)-4-hydroxy-pyrrolidin-2-one;
1-(1,2,3,4-tetrahydro-6,7-dimethoxy-1-napthyl)-pyrrolidin-2-one;
1-(1,2,3,4-tetrahydro-6,7-dimethoxy-2-napthyl)-piperidin-2-one;
1-(1,2,3,4-tetrahydro-6,7-dimethoxy-1-naphtyl)-piperidin-2-one;
1-(1,2,3,4-tetrahydro-6,7-dimethoxy-2-naphtyl)-5-hydroxy-piperidin-2-one;
1-(1,2,3,4,-tetrahydro-6,7-dimethoxy-2-naphtyl)-$\epsilon$-caprolactam;
1-(1,2,3,4-tetrahydro-6,7-dimethoxy-2-naphtyl)-5-hydroxy-$\epsilon$-caprolactam;
1-(1,2,3,4-tetrahydro-6,7-dimethoxy-1-naphtyl)-$\epsilon$-caprolactam;
1-(1,2,3,4-tetrahydro-6,7-dimethoxy-1-naphtyl)-5-hydroxy-$\epsilon$-caprolactam;
1-(1,2,3,4-tetrahydro-1-naphtyl)-4-hydroxy-pyrrolidin-2-one.

3. An orally or parenterally administrable pharmaceutical composition for enhancing the processes of learning and memory which comprises, as active ingredient, a 1,2,3,4-tetrahydronaphtylamine of formula (I)

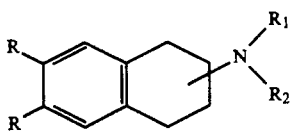

wherein
R is H or OCH$_3$;

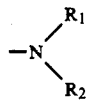

is either at 1 or 2 position
R$_1$ is H;
R$_2$ is selected from:
  L-prolyl, optionally N-substituted with acetyl or carbobenzoxy,
  L-pyroglutamyl,
  (pyrrolidin-2-one-1-yl)acetyl,
  3-carboxy-2-hydroxypropyl;
or R$_1$ and R$_2$ taken together with the nitrogen atom form the ring

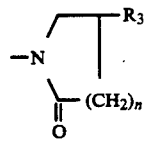

wherein n=1,2,3 and R$_3$=H, OH.

4. The pharmaceutical composition according to claim 3 in unit dosage form, comprising from about 100 to about 500 mg of a compound of formula (I).